(12) United States Patent
Mandecki

(10) Patent No.: US 6,361,950 B1
(45) Date of Patent: Mar. 26, 2002

(54) MULTIPLEX ASSAY FOR NUCLEIC ACIDS EMPLOYING TRANSPONDERS

(75) Inventor: Wlodek Mandecki, Libertyville, IL (US)

(73) Assignee: Pharmaseq, Inc., Monmouth Junction, NJ (US)

( * ) Notice: Subject to any disclaimer, the term of this patent is extended or adjusted under 35 U.S.C. 154(b) by 0 days.

(21) Appl. No.: 09/541,744

(22) Filed: Apr. 3, 2000

Related U.S. Application Data (63) Continuation of application No. 09/158,598, filed on Sep. 22, 1998, which is a continuation of application No. 08/858,363, filed on May 19, 1997, now Pat. No. 6,001,571, which is a continuation of application No. 08/564,851, filed on Nov. 30, 1995, now abandoned.

(51) Int. Cl.[7] ............................. C12Q 1/68; C12P 19/34
(52) U.S. Cl. ........................................ 435/6; 435/91.2
(58) Field of Search ................... 435/16, 91.2; 536/22.1

(56) References Cited

U.S. PATENT DOCUMENTS

| | | |
|---|---|---|
| 4,177,253 A | 12/1979 | Davies et al. |
| 4,297,337 A | 10/1981 | Mansfield et al. |
| 4,452,773 A | 6/1984 | Molday |
| 4,454,234 A | 6/1984 | Czerlinski |
| 4,556,883 A | 12/1985 | Strietzel |
| 4,672,040 A | 6/1987 | Josephson |
| 4,777,145 A | 10/1988 | Luotola et al. |
| 4,778,769 A | 10/1988 | Forrest et al. |
| 4,822,566 A | 4/1989 | Newman |
| 4,857,893 A | 8/1989 | Carroll |
| 4,923,819 A | 5/1990 | Fernandez et al. |
| 4,941,201 A | 7/1990 | Davis |
| 4,965,188 A | 10/1990 | Mullis et al. |
| 5,019,815 A | 5/1991 | Lemelson et al. |
| 5,034,192 A | 7/1991 | Wrighton et al. |
| 5,071,774 A | 12/1991 | Vorpahl et al. |
| 5,153,583 A | 10/1992 | Murdoch |
| 5,200,051 A | 4/1993 | Cozzette et al. |
| 5,202,231 A | 4/1993 | Drmanac et al. |
| 5,214,409 A | 5/1993 | Beigel |
| 5,218,343 A | 6/1993 | Stobbe et al. |
| 5,223,851 A | 6/1993 | Hadden et al. |
| 5,235,326 A | 8/1993 | Beigel et al. |
| 5,245,332 A | 9/1993 | Katzenstein |
| 5,250,944 A | 10/1993 | Urbas et al. |
| 5,252,962 A | 10/1993 | Urbas et al. |
| 5,257,011 A | 10/1993 | Beigel |
| 5,262,772 A | 11/1993 | Urbas et al. |
| 5,266,926 A | 11/1993 | Beigel |
| 5,284,748 A | 2/1994 | Mroczkowski et al. |
| 5,347,263 A | 9/1994 | Carroll et al. |
| 5,422,636 A | 6/1995 | Urbas et al. |
| 5,440,300 A | 8/1995 | Spillman, Jr. |
| 5,445,970 A | 8/1995 | Rohr |
| 5,466,348 A | 11/1995 | Holm-Kennedy |
| 5,481,262 A | 1/1996 | Urbas et al. |
| 5,491,097 A | 2/1996 | Ribi et al. |
| 5,492,806 A | 2/1996 | Drmanac et al. |
| 5,525,464 A | 6/1996 | Drmanac et al. |
| 5,552,270 A | 9/1996 | Khrapko et al. |
| 5,641,634 A | 6/1997 | Mandecki |
| 5,736,332 A | 4/1998 | Mandecki |
| 5,741,462 A | 4/1998 | Nova et al. |
| 5,751,629 A | 5/1998 | Nova et al. |
| 5,770,455 A | 6/1998 | Cargill et al. |
| 5,874,214 A | 2/1999 | Nova et al. |
| 5,925,562 A | 7/1999 | Nova et al. |
| 5,961,923 A | 10/1999 | Nova et al. |
| 5,972,639 A | 10/1999 | Parandoosh |
| 6,017,496 A | 1/2000 | Nova et al. |
| 6,025,129 A | 2/2000 | Nova et al. |

FOREIGN PATENT DOCUMENTS

| | | |
|---|---|---|
| EP | 0526173 A2 | 2/1993 |
| WO | WO90/13666 | 11/1990 |
| WO | WO93/04199 | 3/1993 |
| WO | WO93/21340 | 10/1993 |
| WO | WO96/36436 | 11/1996 |
| WO | WO97/19958 | 6/1997 |
| WO | WO97/20073 | 6/1997 |
| WO | WO97/20074 | 6/1997 |

OTHER PUBLICATIONS

Albretsen, C et al. "Applications of magnetic beads with covalently attached oligonucleotides in hybridization: Isolation and detection of specific measles virus mRNA from a crude cell lysate" *Analytical Biochemistry* (1990) vol. 189, pp. 40–50.

Alper, J. "Drug Discovery on the assembly line" *Science* (Jun. 3, 1994) vol. 264, pp. 1399–1401.

Atkinson, I et al. "A convenient procedure for the synthesis of oligodeoxyribonucleotide affinity columns for the isolation of mRNA", *Nucleic Acids Research*, (1988), vol. 16, No. 13.

Cargill, JF and BE Toyonaga. The Chemical Factory: An Assembly Line Approach to Automated Combinatorial Chemistry on Solid Phase.

Caruthers, MH et al. "Deoxyoligonucleotide synthesis via the phosphoramidite method" Gene Amplification and Analysis, vol. III, (TS Papas et al., eds.) Elsevier Press, Amsterdam.

Drmanac, R et al., "DNA sequence determination by hybridization: a strategy for efficient large–scale sequencing." *Science* (1993) vol. 260, pp. 1649–1652.

(List continued on next page.)

*Primary Examiner*—Eggerton A. Campbell
(74) *Attorney, Agent, or Firm*—Brinks, Hofer, Gilson & Lione (57) ABSTRACT

Disclosed are materials and methods for performing multiplex assays for nucleic acids, in which a transponder is associated with the bead(s) forming the solid phase used in the assay, nucleic acid probes are bound to the surface of the particles, and data concerning the assay is encoded on the transponder. A dedicated read/write device is used to remotely encode or read the data.

11 Claims, 10 Drawing Sheets

OTHER PUBLICATIONS

Flore, F et al. "The Abbott IMx Automated Benchtop Immunochemistry Analyzer System" *Clinical Chemistry* (1998) vol. 34, No. 9.

Ghosh, SS and GF Musso. "Covalent attachment of oligonucleotides to solid supports" *Nucleic Acids Research*, (1987) vol. 15, No. 13.

Gingeras TR et al. "Hybridization properties of immobilized nucleic acids", *Nucleic Acids Research* (1987) vol. 15, No. 13.

Hooft van Hujisduijnen, RAM et al. "A means to reduce the complexity of oligonucleotides encoding degenerate peptides" *Nucleic Acids Research* (1992) vol. 20, No. 4.

Hultman et al. "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Kurstak, E. *Enzyme Immunodiagnostics* (1986) pp. 13–22, Academic Press, NY.

Lam, KS et al. "A new type of synthetic peptide library for identifying ligand–binding activity" *Nature* (Nov. 7, 1991) vol. 354, pp. 82–84.

Maskos, E. et al. "Oligonucleotide hybridisations [sic] on glass supports: a novel linker for oligonucleotide synthesis and hybridisation [sic] properties of oligonucleotides synthesized in situ" *Nucleic Acids Research* (1992) vol. 20, No. 7, pp. 1679–1684.

McHugh, T. "Flow Microsphere Immunoassay for the Quantative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem. Soc.* (1995) vol. 117, pp. 10787–10788.

Morrissey, NE et al. "Modified method for determining carcinoembryonic antigen in the presence of human anti–murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 210, pp. 2289–2291.

Pease, AC et al. "Light–generated oligonucleotide arrays for rapid DNA sequence analysis" *Proc. Natl. Acad. Sci.* (1994), vol. 91, pp. 5022–5026.

Pierce catalog. (1994) pp. T159, T314–T315, Rockford, Illinois US.

Principles And Practice Of Immunoassay, Chapter 5, "Immunoassay Design And Optimizatization".

Principles And Practice Of Immunoassay, Chapter 13, "Heterogeneous Fluoroimmunoassay".

Sambrook et al. *Molecular Clonig: A laboratory manual* (1989) $2^{nd}$ ed. Lake Press, NY.

Service R. "Radio tags speed compound synthesis" *Science*, (Oct. 27, 1995) vol. 270, p. 577.

Sproat, BS and DM Brown "A new linkage for solid phase synthesis of oligodeoxyribonucleotides" *Nucleic Acids Research* (1985) vol. 13, pp. 2979–2987.

Urdea et al "A comparsion of non–radioisotopic hybridization assay methods using fluorescent, chemiluminescent and enzyme labeled synthetic oligodeoxyribonucleotide probes" *Nucleic Acids Research*, (1988) vol. 16, No. 11 pp. 4937–4956.

Guo et al. "Direct Fluorescence Analysis of Genetic Polymorphism by Hybridization With Oligonucleotide Arrays on Glass Support" *Nucleic Acids Research*, (1994) vol. 22, pp. 2456–2465.

MULTIPLEX ASSAY FOR NUCLEIC ACIDS EMPLOYING TRANSPONDERS

This application is a continuation of application Ser. No. 09/158,598, filed Sep. 22, 1998, which is a continuation of Ser. No. 08/858,363, filed May 19, 1997 now U.S. Pat. No. 6,001,571, which is a continuation of Ser. No. 08/564,851, filed Nov. 30, 1995 now abandoned.

BACKGROUND OF THE INVENTION

This invention relates to materials and methods for detecting nucleic acids in samples and, more particularly, to solid phase assays wherein transponders are associated with the beads constituting the solid phase, nucleic acid probes are bound to the surface of the particles and data concerning the assay is encoded on the transponders.

Solid phase assays have been used to determine the presence of nucleic acids, including deoxyribonucleic acids (DNA), ribonucleic acids (RNA) and their modified forms. Solid-phase assays can be applied to nucleic acids either in simple buffers, or in biological fluids, such as blood, serum, plasma, saliva, urine, tissue homogenates, and many others.

In solid phase assays, small beads, or microparticles, are used as the solid phase to capture the analyte. Solid-phase microparticles can be made of different materials, such as glass, plastic, latex, depending on the particular application. Some beads are made of ferromagnetic materials to facilitate their separation from complex suspensions or mixtures.

In conventional solid-phase assays, the solid phase mainly aids in separating molecules that bind to the solid phase from molecules that do not bind to the solid phase. Separation can be facilitated by gravity, centrifugation, filtration, magnetism, immobilization of molecules onto the surface of the vessel, etc. The separation may be performed either in a single step in the assay or, more often, in multiple steps.

Often, there is a need to perform two or more different assays on the same sample, most of the time in a single vessel and at about the same time. Such assays are known in the art as multiplex assays. Multiplex assays are performed to determine simultaneously the presence or concentration of more than one molecule in the sample being analyzed, or alternatively, several characteristics of a single molecule, such as, the presence of several epitopes on a single protein molecule.

One problem with conventional multiplex assays is that they typically cannot detect more than about five analytes simultaneously, because of difficulties with simultaneous detection and differentiation of more than about five analytes. In other words, the number of different analytes that may be assayed in a single solid phase assay is limited by the solid phase.

SUMMARY OF THE INVENTION

The present invention overcomes many of these problems by employing transponders associated with the solid phase beads to index the particles constituting the solid phase. Thus, each individual solid phase particle can be assigned a unique index number electronically encoded inside the particle, that can be retrieved at any time, e.g., at one time during the assay, at multiple times during the assay, or continuously during the assay. The index number may define the nucleotide sequence of the oligonucleotide deposited on the surface of the particle, the catalog number of a DNA fragment deposited on the particle, index numbers of chemical steps which were involved in the chemical synthesis of an oligonucleotide bound to the particle, or some other relevant characteristics of the deposited molecules.

In an electronically-indexed multiplex assay of this invention, two or more classes of transponders, each encoded with a different index number and constructed to bind a different nucleic acid sequence, are incubated with the sample in a single vessel. After necessary washes, incubations and additions are performed, the solid phase is analyzed to detect a label indicative of binding of nucleic acid in the sample to the oligonucleotide on the transponder, such as fluorescence, color, radioactivity or the like. Solid phase analysis is either preceded or followed by decoding of the index numbers programmed on the transponders.

Determination of the label and decoding of the memory of the transponder can be done manually on two different instruments, such as a fluorometer and a dedicated scanner, although a single automated instrument that would perform both functions may be used. Such an instrument can be a modified fluorometer in which the scanner is mounted in the proximity of the fluorometer readout window, and reading the sample fluorescence and decoding the transponder are coordinated by a central computer. In addition, such an instrument can be equipped with an automated transport system for transponders.

In one aspect, the present invention provides an electronically-indexed solid phase particle for use in solid phase assays for nucleic acids, comprising a transponder and a nucleic acid sequence attached to the transponder.

In another aspect, the present invention provides a method for detecting nucleic acids in a sample, using solid phase particles having transponders.

In another aspect, the present invention provides kits for detecting nucleic acids in samples, comprising assay vessels, at least one transponder having a nucleic acid probe bound to the transponder, and a labelled reagent to detect binding of sample nucleic acids to the probe.

DETAILED DESCRIPTION OF THE INVENTION

Figure 1:
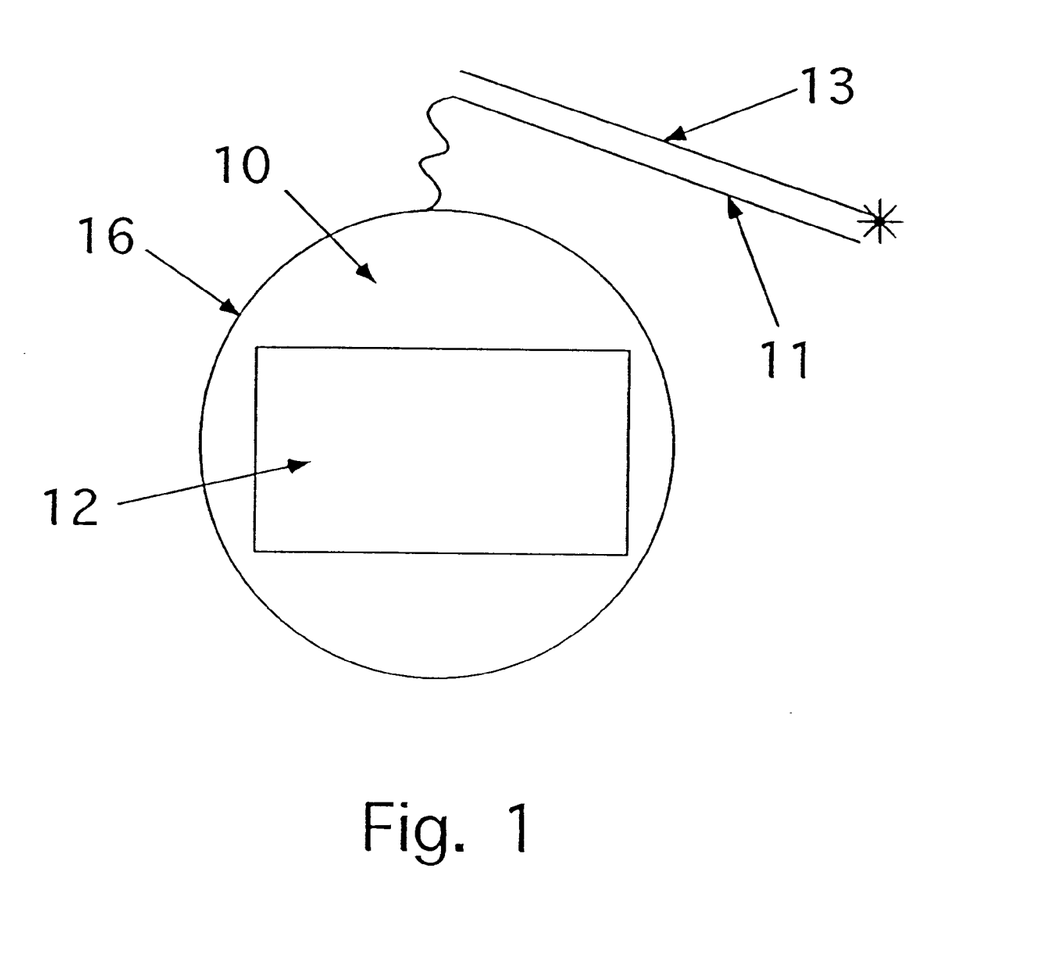
FIG. 1 is a schematic representation of a simple assay of this invention.

FIG. 1 depicts a simple assay of the invention. A solid phase particle 10, with a transponder 12 is derivatized by attaching an oligonucleotide probe 11 to the outer surface 16 of the particle 10. Information concerning the assay, e.g., an index number identifying the patient, is encoded on the transponder, either by the manufacturer of transponder, or by the user with a remote read/write scanner device (not shown). Sample containing target nucleic acid 13 is treated to label all of the nucleic acid therein. The derivatized particle 10 is placed in a sample, and the sample is heated to cause nucleic acids to dissociate. The sample is then cooled under controlled conditions to cause the nucleic acids to anneal. Target nucleic acids 13 complementary to the oligonucleotide probe 11 anneal to the probe 11. The particle 10 is thoroughly washed to remove unbound components. The labelled target nucleic acid 13 bound to the probe 11 is detected with a fluorometer to identify those transponders 12 that have target nucleic acid 13 bound thereto, and the transponder 12 is decoded using the scanner device (not shown) to retrieve the information encoded thereon.

The detection and decoding steps may be done separately or may be done simultaneously. Alternatively, the particles of many samples may be pooled into a vessel in no particular order with mixing allowed, and passed through a reader (not shown) that determines and records the fluorescence and, at the same time, decodes the index number recorded in the transponder 12. It is important to note that when encoding or reading data on a transponder, other transponders must be shielded by a metal barrier or other means to prevent the electromagnetic radiation from reaching such "non-target" transponders.

Figure 1A:
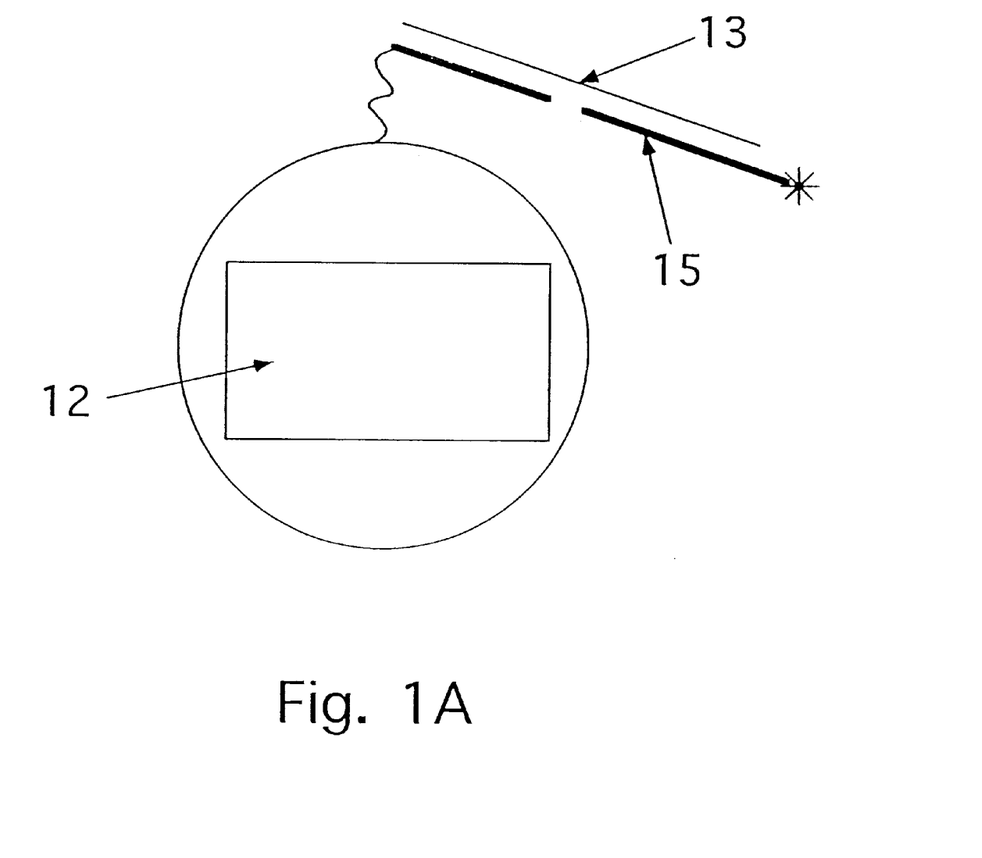
FIG. 1A is a schematic representation of a simple assay of this invention utilizing an alternative labelling technique.

In an alternative labelling technique, depicted in FIG. 1A, a second fluorescent-labelled oligonucleotide probe 15 complementary to a second sequence of the target nucleic acid 13 is added to the sample mixture, to specifically label transponders 12 to which target nucleic acids 13 have bound.

Figure 2:
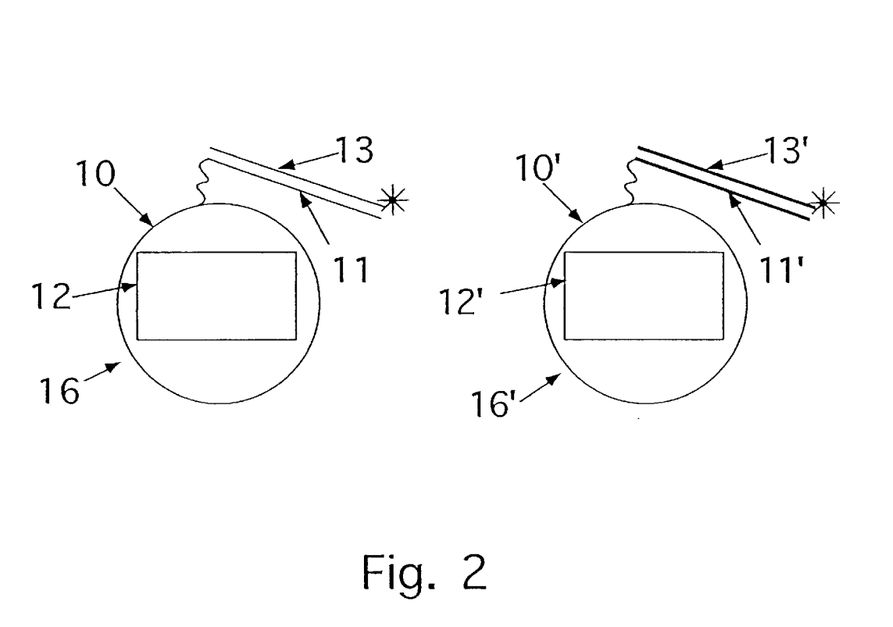
FIG. 2 is a schematic representation of a multiplex assay of this invention.

A multiplex assay according to this invention is conducted in a similar manner, as depicted in FIG. 2, with two or more transponders 12 in each assay vessel (not shown) to detect more than one target nucleic acid 13 simultaneously. The transponders 12 are divided into two or more classes 12 and 12', each class having a distinct index number identifying the class, and each class having a different oligonucleotide probe 11 and 11' bound to the surface 16 of the particle 10 and 10'. Using each class of transponder 12, 12' is separately encoded, either by the manufacturer or by the user with a read/write scanner device (not shown), with an index number to identify, e.g., the sequence of the probe 11 bound to the surface 16 of the particle 10. Again, it is necessary to shield other, non-target transponders during the encoding process. The transponders 12, 12' are added to a sample, and the sample is heated to cause nucleic acids to dissociate. The sample is then cooled under controlled conditions to cause the nucleic acids to re-anneal. Target nucleic acid 13, 13' complementary to the respective probes 11, 11' anneals to the probes 11, 11'. The transponders 12, 12' are then washed thoroughly to remove unbound sample components and reagents. The labelled probes 15, 15' are detected with a fluorometer to identify those transponders 12, 12' that have target nucleic acids 13, 13' bound thereto, and the transponder 12, 12' is decoded using the scanner device (not shown) to retrieve the information encoded thereon. The detection and decoding steps may be done separately or may be done simultaneously. Alternatively, the particles 10, 10' may be pooled into a vessel in no particular order with mixing allowed, and passed through a reader (not shown) that determines and records the fluorescence and, at the same time, decodes the index number recorded in the transponder 12, 12'.

Figure 2A:
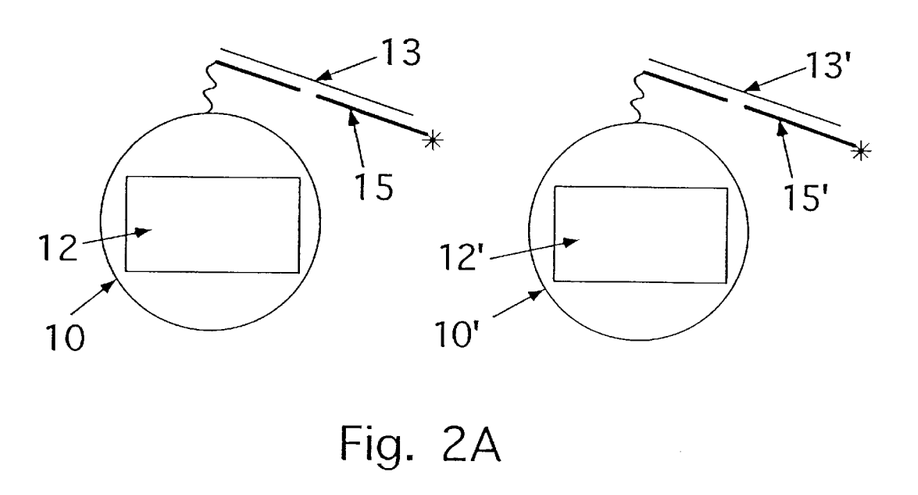
FIG. 2A is a schematic representation of a multiplex assay of this invention utilizing an alternative labelling technique.

In an alternative labelling technique, depicted in FIG. 2A, second fluorescent-labelled oligonucleotide probes 15, 15' that bind to second sequences of the target nucleic acids 13, 13' are added to the sample vessel to bind to the target nucleic acids 13, 13'. Alternatively, the label may be a radioisotope, such as $^{32}P$, $^{35}S$, $^{125}I$, and the like. The label may also be a chemiluminescent label, such as a luminol derivative or an acridinium ester, that emits light upon oxidation of a substrate. The label may be an enzyme, such as alkaline phosphatase, catalyzing a reaction employing a precipitating fluorogenic substrate, e.g., attophos (JBL Scientific, San Luis Obispo, Calif.), a precipitating chromogenic substrate, e.g., 5-bromo-4-chloro-3-indolyl phosphate), or a chemiluminescent substrate, e.g., adamantyl 1,2-dioxetane phosphate (Tropix, New Bedford, Mass.). Finally, the label may be a bioluminescent enzyme such as luciferin.

The present multiplex assay can be applied to different types of nucleic acids, DNA, RNA, modified nucleic acids and analogs of nucleic acids (in particular protein-nucleic acids, PNAs). The analyte can be a complex of biomolecules, such as a virus particle, a nucleic acid-protein complex, or a nucleic acid-hapten complex. It is also evident that the target nucleic acid analyte, which is being monitored, can be present in a variety of forms, such as a solution in a simple buffer, but also in a complex biological fluid, such as blood, serum, urine, saliva, and many others. The target nucleic acid can be mixed with many other analytes that are simultaneously being assayed in the multiplex format. The purity of the nucleic acid deposited as a primary layer on the surface of the transponder can vary as well, from unpurified, partially purified to pure compounds.

The nucleic acids, their complexes and aggregates can be deposited as a primary layer on the surface of the transponder by a variety of means, including chemical conjugation to an active group on the support, direct chemical synthesis, combinatorial synthesis, adhesion or non-specific binding through hydrophobic interactions. The nucleic acid deposited as a primary layer on the surface of the transponder can be made in vivo, in an enzymatic reaction in vitro, or chemically synthesized. A preferred example of a product of an enzymatic reaction in vitro is the nucleic acid obtained from the polymerase chain reaction (PCR).

Figure 3:
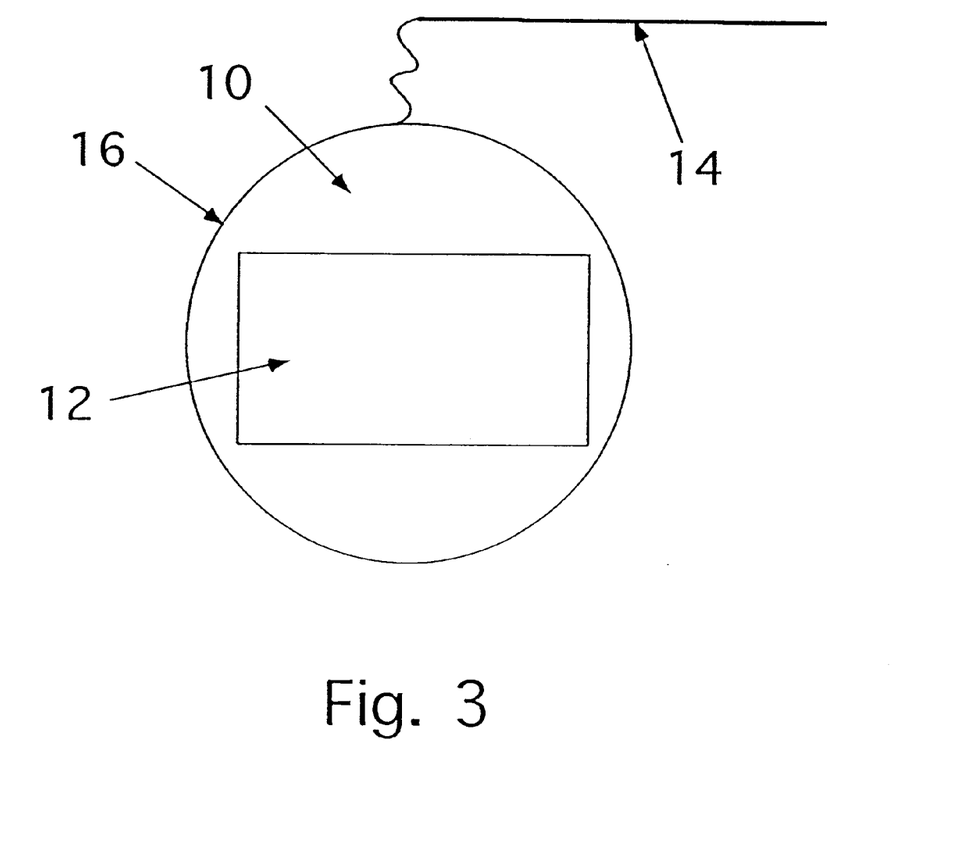
FIG. 3 is a diagram of a solid phase particle with a transponder, and a primary layer of a nucleic acid sequence attached to the surface thereof.

FIG. 3 depicts a solid phase particle 10 of the present invention, having a transponder 12, and a primary layer 14 of an oligonucleotide probe attached to the outer surface 16 of the particle 10.

A transponder is a radio transmitter-receiver activated for transmission of data by reception of a predetermined signal, and may also be referred to as a microtransponder, radiotransponder, radio tag, transceiver, etc. The signal comes from a dedicated scanner that also receives and processes the data sent by the transponder. The scanner function can be combined with the write function, i.e., the process of encoding the data on the transponder. Such a combination instrument is referred to as a scanner read/write device. An advantage of the transponder-scanner systems is that the two units are not electrically connected by wire, but are coupled inductively, i.e. by the use of electromagnetic radiation, typically in the range from 5–1,000 kHz, but also up to 1 GHz and higher.

Figure 4:
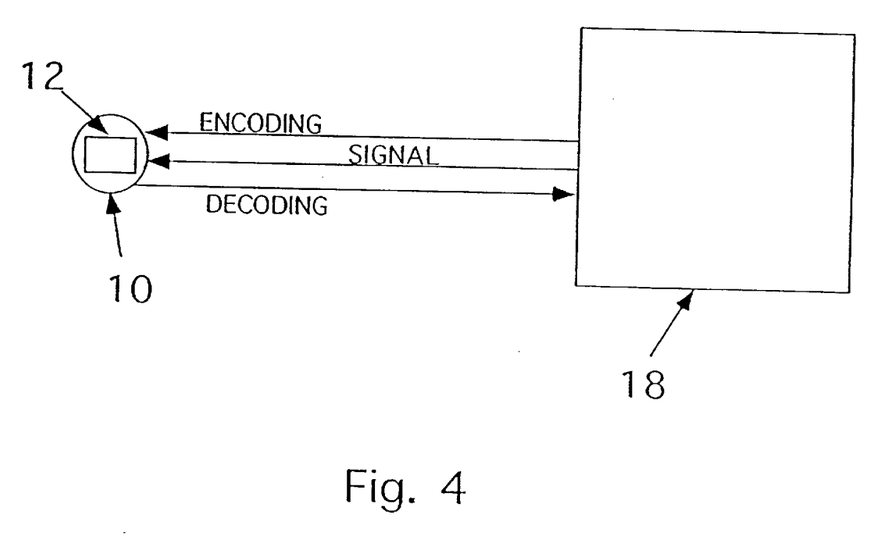
FIG. 4 is a schematic diagram of the signal pathway for encoding and encoding data on the transponders.

FIG. 4 is a flow chart illustrating the communication between the transponder 12 and a remote scanner read/write device 18. The transponder 12 is encoded and/or decoded with data sent by electromagnetic waves from a remote scanner read/write device 18, unless the transponders 12 have been encoded by the manufacturer. After the assay steps are completed, the beads 10 are analyzed to detect the presence of a label indicative of binding of analyte and the transponders 12 are decoded. The scanner 18 sends a signal to the transponder 12. In response to the signal, the transponder 12 transmits the encoded data to the scanner 18.

Some transponders similar to those used in the present invention are available commercially. BioMedic Data Systems Inc. (BMDS, 255 West Spring Valley Ave., Maywood, N.J.) manufactures a programmable transponder for use in laboratory animal identification. The transponder is implanted in the body of an animal, such as a mouse. The transponder is glass-encapsulated to protect the electronics inside the transponder from the environment. One of the transponders manufactured by this corporation, model IPTT-100, has dimensions of 14×2.2×2.2 mm and weight of 120 mg. The transponder is user-programmable with up to 16 alphanumeric characters, the 16th letter programmable independently of the other 15 letters, and has a built-in temperature sensor as well. The electronic animal monitoring system (ELAMS) includes also a scanner read/write system, such as the DAS-501 console system, to encode or read data on/from the transponder. The construction of the transponder and scanner is described in U.S. Pat. Nos. 5,250,944, 5,252,962 and 5,262,772, the disclosures of which are incorporated herein by reference. Other similar transponder-scanner systems include a multi-memory electronic identification tag (U.S. Pat. No. 5,257,011) by AVID Corporation (Norco, Calif.) and a system made by TEMIC-Telefunken (Eching, Germany). AVID's transponder has dimensions of 1 mm×1 mm×11 mm, and can encode 96 bits of information, programmable by the user. The present invention can be practiced with different transponders, which might be of different dimensions and have different electronic memory capacity.

The commercially available transponders are relatively large in size. The speed at which the transponders may be decoded is limited by the carrier frequency and the method of transmitting the data. In typical signal transmission schemes, the data are encoded by modulating either the amplitude, frequency or phase of the carrier. Depending on the modulation method chosen, compression schemes, transmission environment, noise and other factors, the rate of the signal transmission is within two orders of magnitude of the carrier frequency. For example, a carrier frequency of 1,000 Hz corresponds to rates of 10 to 100,000 bits per second (bps). At the rate of 10,000 bps the transmission of 100 bits will take 0.01 sec. The carrier frequency can be several orders of magnitude higher than 1,000 Hz, so the transmission rates can be proportionally higher as well.

Therefore, the limiting factor in the screening process is the speed at which the transport mechanism carries the transponders through the read window of the fluorometer/scanner device. The rate of movement of small particles or cells is $10^4$–$10^5$ per second in state-of-the-art flow cytometers. A flow cytometer may be used to practice the present invention, if two conditions are met: (1) the transponders are small enough to pass through the flow chamber, and (2) the design of the flow chamber of the flow cytometer is modified to include an antenna and a read/write scanner device for collecting the electromagnetic radiation emitted by transponders.

Figure 5:
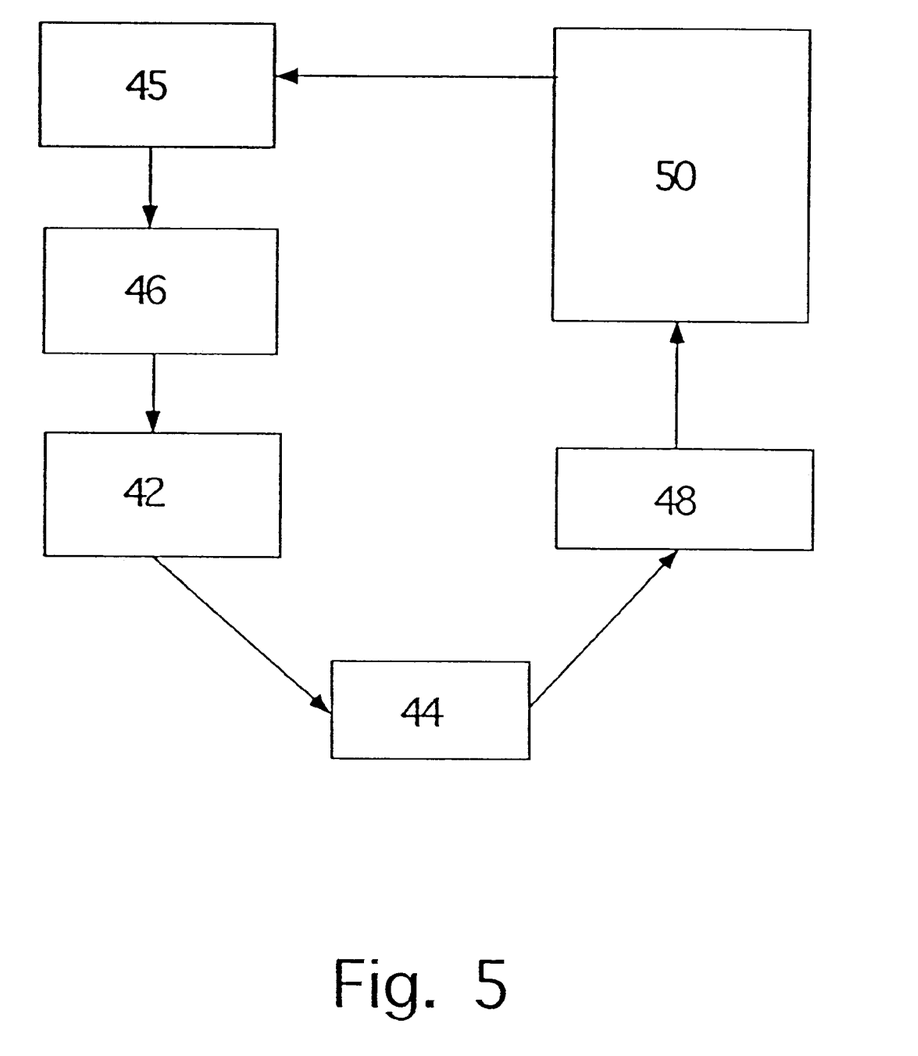
FIG. 5 is a schematic representation of a miniature transponder.
Figure 6:
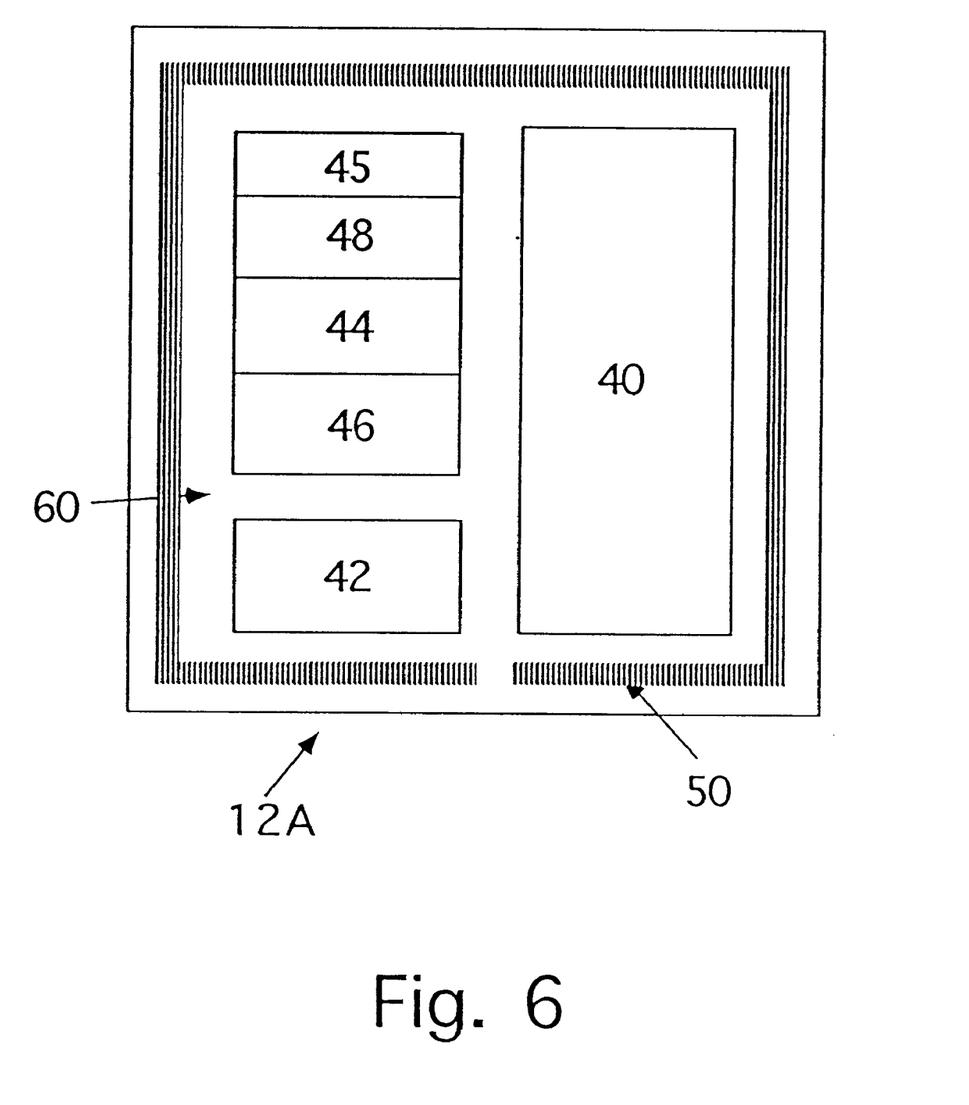
FIG. 6 is a plan view of a miniature transponder.

A miniature transponder is depicted in FIGS. 5 and 6. The source of the electrical power for the transponder 12a is at least one photovoltaic cell 40 within the transponder 12a, illuminated by light, preferably from a laser (not shown). The same light also induces the fluorescence of fluorogenic molecules immobilized on the surface of the transponder 12a. The transponder 12a includes a memory element 42 that may be of the EEPROM type, or the ROM type. The contents of the memory is converted from the digital form to the analog form by a Digital-to-Analog converter 44 mounted on the transponder 12a. The signal is amplified by an amplifier 45, mixed with the carrier signal produced by an oscillator 48, and emitted to the outside of the transponder 12a by an antenna 50.

In an alternative embodiment, the signal from the scanner (not shown) is transmitted to the transponder 12a by modulating the intensity of the light illuminating the transponder 12a, which also serves to actuate the photovoltaic cell power source 40.

The contents of the miniature transponder memory can be permanently encoded during the manufacturing process of the transponder, different batches of transponders being differently encoded. Preferably, the memory of the transponder is user-programmable, and is encoded by the user just before, during, or just after the biological material is deposited on the surface of the transponder. A user-programmable transponder 12a must have the "write" feature enabled by the antenna 50, amplifier 44 and the Analog-to-Digital converter 46 manufactured on the transponder 12a, as well as the dedicated scanner/write device 27.

The advantages of the transponder of FIGS. 5 and 6 are several-fold. First, the transponder dimensions are reduced relative to a conventional transponder, because most of the volume of a conventional transponder is occupied by the solenoid. The design discussed above will enable the production of cubic transponders on the order of 0.01 to 1.0 mm as measured along a side of the cube, preferably 0.05 to 0.2 mm.

Second, a large number of transponders can be manufactured on a single silicon wafer. As depicted schematically in FIG. 6, a silicon wafer 60 is simply cut to yield active transponders 12a. Third, the transponder, according the new design, will not need the glass capsule as an enclosure, further reducing the size of the transponder. Silicone dioxide ($SiO_2$) would constitute a significant portion of the surface of the transponder, and $SiO_2$ has chemical properties like glass in terms that allow derivatization or immobilization of biomolecules. Alternatively, the transponder may be coated with a variety of materials, including plastic, latex and the like.

Finally, most importantly, the narrow focus of the beam of the laser light would enable only one transponder to be active at a time during the decoding step, significantly reducing noise level. Advanced user-programmability is desirable as well, and preferably, various memory registers are addressable independently, i.e., writing in one register does not erase the contents of other registers.

Figure 7:
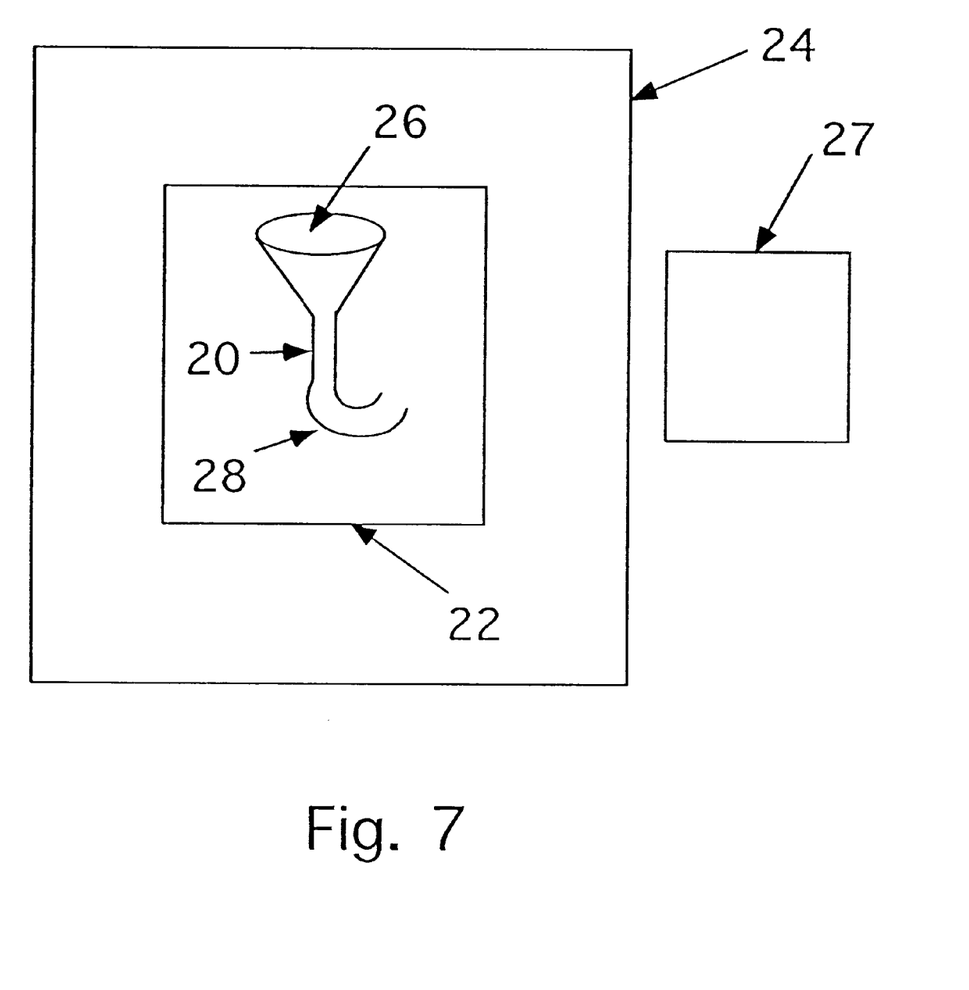
FIG. 7 is a plan view of a transport system/analytical instrument for implementing this invention.

FIG. 7 shows the analytical instrumentation and transport system used in an embodiment of the present invention. A quartz tube 20 is mounted in the readout window 22 of a fluorometer 24. The quartz tube 20 is connected to a metal funnel 26. The length of the quartz tube 20 is similar to the dimensions of the transponder 12. Transponders 12 are fed into the metal funnel 26, and pass from the funnel 26 into the quartz tube 20, where the fluorescence is read by the fluorometer 24 and the transponder 12 is decoded by the scanner 27, and then exit through a metal tube 28 and are conducted to a collection vessel (not shown). The metal funnel 26 and metal tube 28 are made of metal shield transponders 12 outside of the read window 22 by shielding from the electromagnetic signal from the scanner 27. This shielding prevents the scanner signal from reaching more than one transponder 12, causing multiple transponders 12 to be decoded.

Minimal modification of the fluorometer 24 would be needed in the vicinity of the location that the tube occupies at the readout moment to allow for positioning of the transponder reading device. To assure compatibility with existing assays, the glass surrounding the transponder could be coated or replaced with the type of plastic currently used to manufacture beads.

Figure 8:
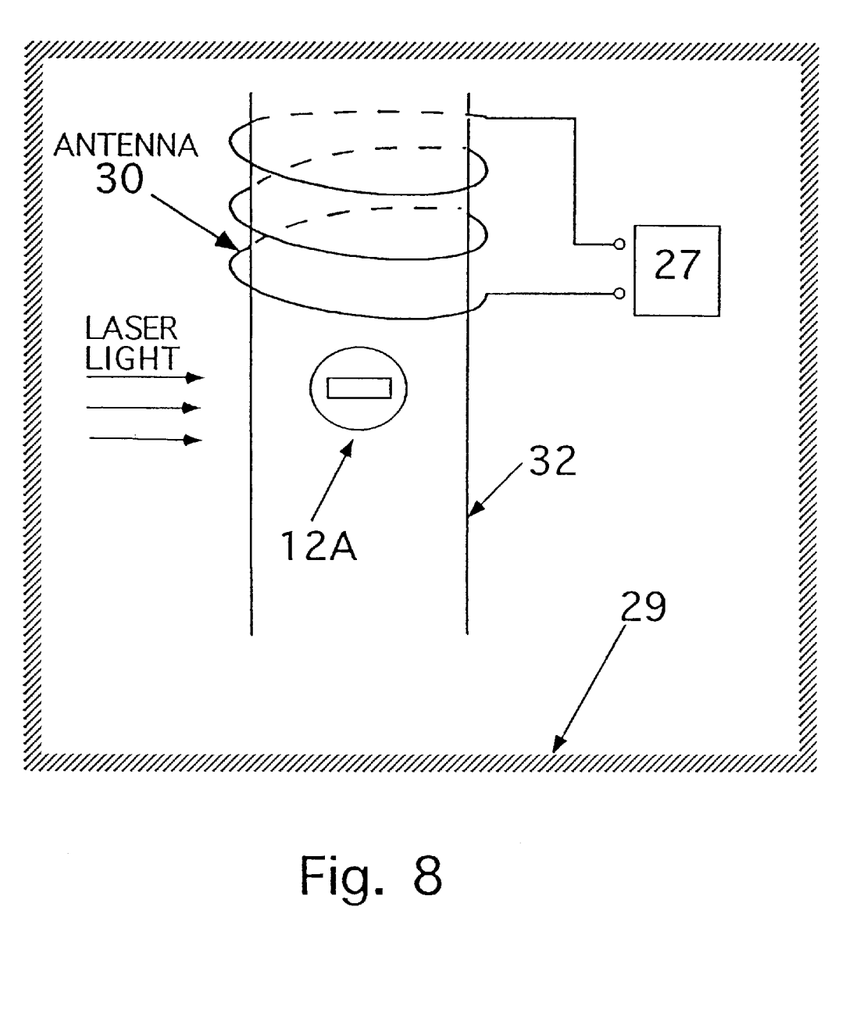
FIG. 8 is a plan view of modified flow cytometer for high speed analysis of solid phase particles of this invention.

In a preferred design, depicted in FIG. 8, a metal coil antenna 30 is wrapped around the flow cell 32 of a flow cytometer 29. The transponders 12 pass through the flow cell 32, and are decoded by the scanner device 27. The signal carrying the data sent from the transponders 12 is processed by the scanning device 27. As the transponders 12 are decoded, fluorescence from the transponders 12 is detected and analyzed by the flow cytometer 29.

EXAMPLE 1

Multiplex DNA-Based Assay on Transponders Employing DNA Synthesized on the Solid Support The glass outer surface of the transponders is first derivatized by an aminoalkylsilane treatment. The transponders (e.g., IPTT-100, BMDS) are cleaned by washing with xylene, followed by a 70% ethanol rinse and air drying. The transponders are then submerged for about 30 seconds in a 2% solution of aminopropyltriethoxysilane (Cat.# A3648, Sigma, St. Louis, Mo.) in dry acetone. The transponders are then sequentially rinsed with dry acetone and distilled water, and then air dried. This procedure is described in the Pierce catalog (pp. T314–T315 of the 1994 catalog, Pierce, Rockford, Ill.).

Nucleic acid probes are then covalently linked to the aminoalkylsilane-treated glass by direct chemical synthesis on the glass support. A thymidine-derivatized support containing a stable nucleoside-urethane linkage is prepared, in which 5'-dimethoxytrityl thymidine is reacted with one equivalent of tolylene-2,6-diisocyanate in the presence of one equivalent of N-ethyldiisopropylamine as a catalyst in pyridine/1,2-dichloroethane to generate the monoisocyanate. The monoisocyanate is not isolated, but is reacted directly with the aminopropyltriethoxysilane-derivatized glass surface of the transponders. The procedure is described in detail in B. S. Sproat and D. M. Brown, A new linkage for solid phase synthesis of oligodeoxyribonucleotides, Nucleic Acids Res. 13, 2979–2987, 1985.

The thymidine-derivatized support containing a stable nucleoside-urethane linkage is used directly for the chemical synthesis of oligodeoxynucleotides by manual synthesis on sintered funnels using standard phosphoramidite-based DNA synthesis reagents, as described in Caruthers, M. H. et al., Deoxyoligonucleotide Synthesis Via The Phosphoramidite Method, Gene Amplification and Analysis, Vol. III (T. S. Papas et al., Eds., Elsevier/North Holland, Amsterdam). The thymidine-urethane linker is resistant to cleavage with base during deprotection, and the resulting product is the deprotected oligonucleotide attached to the glass surface of the transponder through the urethane-thymidilate linker.

The following oligodeoxynucleotide reagents are prepared Sequence 1 and sequence 2 do not exhibit self-complementarity, are 15 nt long, and are linked to the transponders through a spacer, which is an oligonucleotide having the $(dT)_{10}$ sequence. Oligonucleotides C and D are derivatized at the 5'-end with fluorescein. The sequences are as follows:

transponder-oligonucleotide A: 5'-spacer-sequence1
transponder-oligonucleotide B: 5'-spacer-sequence2
oligonucleotide C: 5'-fluorescein-sequence1complement
oligonucleotide D: 5'-fluorescein-sequence2complement Four assay tubes are prepared and labeled 1, 2, 3 and 4, each assay tube to accommodate two transponders, one transponder carrying oligonucleotide A and the second transponder carrying oligonucleotide B. The transponders are electronically encoded with two alphanumeric characters, namely A1,A2,A3,A4 and B1,B2,B3,B4, where the letter corresponded to the oligonucleotide used to derivatize the transponder, and the digit gave the test tube number into which the given transponder is placed. Thus tube 1 contains transponders A1 and B1; tube 2—A2 and B2; tube 3, A3 and B3; and tube 4, A4 and B4, all immersed in 50 mM Tris-HCl buffer (pH 7.5). Four analytes, X,Y,Z and W, are prepared, as follows. Analyte X contains oligonucleotide C and oligonucleotide D; Y contains oligonucleotide C only, Z contained oligonucleotide D only, and analyte W does not contain any oligonucleotides. The analyte solutions are prepared in 50 mM Tris-HCl (pH 7.5). The concentration of each given oligonucleotide in the analytes X, Y and Z is 10 nM to 10 $\mu$M. After the four tubes are emptied of buffer, but retain the transponders, 2 mls of X,Y,Z and W analyte are added to tubes 1, 2, 3 and 4, respectively. The tubes are heated to 90° C., and slowly cooled to room temperature. Then the transponders are rinsed three times with the buffer. The fluorescence of each transponder is measured on a FluorImager instrument (Molecular Dynamics).

EXAMPLE 2

Multiplex DNA-Based Assay on Transponders Employing Conjugation of Oligonucleotides to Solid Support Precleaned transponders (IPTT-100, BMDS) are immersed in a 1% 3-aminopropyltrimethoxysilane solution (Aldrich Chemical, Milwaukee, Wis.) in 95% acetone/water for 2 minutes, washed extensively with acetone (10 washes, 5 minutes each) and dried (110° C. for 45 minutes). The transponders are then treated for 2 hours with 1,4-phenylene diisothiocyanate (Aldrich) (PDC, 0.2% solution in 10% pyridine/dimethyl formamide). The transponders are washed with methanol and acetone and stored at 4° C. in an anhydrous environment. The 5'-amino-modified oligonucleotides to be immobilized on the glass support are dissolved in 100 mM sodium carbonate/bicarbonate buffer (pH 9.0) at a concentration of 2 mM, and a 2 $\mu$l aliquot is applied directly to the PDC-derivatized transponders and incubated at 37° C. in a closed vessel for 2 hours. The transponders are then washed with $NH_4OH$, three times with water and air dried at room temperature. This derivatization procedure is based on a protocol described in Guo et al. (Direct Fluorescence Analysis Of Genetic Polymorphism By Hybridization With Oligonucleotide Arrays On Glass Support. Nucleic Acids Res. 22, 5456–5465, 1994).

The following oligodeoxynucleotide reagents are prepared. Sequence1 and sequence2 are 15 nt long, and are linked to the transponders through an oligonucleotide spacer having the $(dT)_{10}$ sequence. Oligonucleotides C and D are derivatized at the 5'-end with fluorescein. The sequences are as follows:

transponder-oligonucleotide A: 5'-spacer-sequence1
transponder-oligonucleotide B: 5'-spacer-sequence2
oligonucleotide C: 5'-fluorescein-sequence1complement
oligonucleotide D: 5'-fluorescein-sequence2complement Four assay tubes are prepared and labeled 1, 2, 3 and 4, each tube to accommodate two transponders, one transponder carrying oligonucleotide A and the second transponder carrying oligonucleotide B. The transponders are electronically encoded with two alphanumeric characters, namely A1,A2,A3,A4 and B1,B2,B3,B4, where the letter corresponded to the oligonucleotide used to derivatize the transponder, and the digit gave the test tube number into which the given transponder is placed. Thus tube 1, contains transponders A1 and B1; tube 2—A2 and B2; tube 3, A3 and B3; and tube 4, A4 and B4, all immersed in 50 mM Tris-HCl buffer (pH 7.5). Four analytes, X,Y,Z and W, are prepared, as follows. Analyte X contains oligonucleotide C and oligonucleotide D; Y contains oligonucleotide C only, Z contained oligonucleotide D only, and analyte W does not contain any oligonucleotides. The buffer is 50 mM Tris-HCl (pH 7.5). The concentration of each given oligonucleotide in the analytes X, Y and Z is 10 µM. After the four tubes are emptied of buffer, but retain the transponders, 2 mls of X,Y,Z and W analyte are added to tube 1,2,3 and 4, respectively. The tubes are heated to 90° C., and slowly cooled to room temperature. Then the transponders are rinsed three times with the buffer. The fluorescence of each transponder is measured on a Fluorimager (Molecular Dynamics).

EXAMPLE 3

Conjugation of Streptavidin to the Glass Surface of Transponders

The outside glass surface of transponders (IPTT-100, BMDS) is derivatized through the aminoalkylsilane treatment outlined above, and a linker is attached to the aminoalkylsilane-treated glass. A variety of methods can be used, as reviewed in Enzyme Immunodiagnostics, E. Kurstak, Academic Press, New York, 1986, pp. 13–22. This procedure a homobifunctional NHS-ester cross-linker, $BS^3$, bis(sulfosuccinimidyl)suberate (Pierce Cat.# 21579, described on p. T159 of the 1994 Pierce catalog).

The transponders are immersed in the 10 mM solution of $BS^3$ in 100 mM phosphate buffer (pH 7.0–7.4) for 5 to 60 minutes at room temperature, and the transponders are rinsed with water. A 10–100 µM streptavidin solution in 100 mM phosphate buffer (pH 7.4–8.0) is prepared. The transponders are submerged in the streptavidin solution and incubated at room temperature for 2–3 hours. The transponders are rinsed three times with 100 mM phosphate buffer (pH 7.4–8.0). The unreacted sites on the glass are blocked by incubating in Blocker BLOTTO in PBS (phosphate-buffered saline) (Pierce, Cat.# 37526) for 2 hrs. The transponders are rinsed three times with 100 mM phosphate buffer (pH 7.4–8.0), and stored in this buffer at 4° C.

EXAMPLE 4

Detection of a Point Mutation in the N-ras Gene

Point Mutations in the N-ras Gene are frequently observed in various hematological and solid tumors. A well-characterized mutation is a G→C mutation in the first position of the 12th codon of the N-ras gene. The present example provides a method to detect this mutation implementing transponders.

The sequence of the first exon of the N-ras gene is given in Table 1. The glass surface of transponders (IPTT-100, BMDS) used in this example is derivatized with streptavidin using the conjugation method described in Example 3. The following oligodeoxynucleotides are chemically synthesized:

(1) GACTGAGTACAAACTGGTGG, corresponding to residues 3–22 of exon 1;
(2) CTCTATGGTGGGATCATATT-biotin, corresponding to residues 111 91;
(3) AACTGGTGGTGGTTGGAGCA, corresponding to residues 14–33, Oligonucleotide (2) is biotinylated at the 5'end. These sequences were previously used to perform mini-sequencing using scintillating microplates by Ihalainen et al. (BioTechniques, 16, 938–943, 1994). Cellular DNA from patient samples is purified using the standard Blin and Safford procedure (Sambrook et al., 1989, Molecular Cloning: A Laboratory Manual, 2nd Edition, Cold Spring Harbor Laboratory Press, Cold Spring Harbor, N.Y.). PCR amplification of DNA using primers (1) and (2) is done on the Perkin-Elmer Cycler 9600, employing 50 cycles of amplification. Each cycle involved a 1 minute denaturation at 94° C., 1 minute annealing at 55° C. and 1 minute chain extension at 72° C. in a final volume of 100 µl. The single DNA strand carrying biotin is captured on two transponders conjugated to streptavidin by incubating the product of the PCR reaction with the transponders in a buffer containing 150 mM NaCl, 20 mM sodium phosphate (pH 7.4) and 0.1% Tween-20 at 37° C. with gentle shaking for 90 minutes. The bound PCR product was denatured with 50 mM NaOH for 5 minutes at room temperature. The transponders are then washed extensively 3–5 times with a buffer (40 mM Tris-HCl, pH 8.8, 1 mM EDTA, 50 mM NaCl, 0.1% Tween-20). The patient name, consisting of six alphanumeric characters, is encoded on the two transponders using a dedicated read-write scanner.

The diagnostic chain extension reaction is configured for one transponder as follows. The primer, oligonucleotide (3) is at a final concentration of 0.4 M, $^3$H dCTP or $^3$H dGTP (Amersham) at 0.2 µM, and 4 units of Taq polymerase, in a final volume of 1 ml of a buffer containing 50 mM KCl, 10 mM Tris-HCl (pH 9.0 at 25° C.), 0.1% Triton X-100, 4 mM MgCl. The final volume and the test tube type are adjusted depending on the number of transponders so that the whole surface of the transponders is covered with buffer. The reaction is incubated at 55° C. for 10 minutes with gentle shaking.

To determine whether the mutation is present, transponders are used in two DNA chain extension reactions. The first reaction contains $^3$H dCTP and no other dNTPs, the second one contains $^3$H dCTP and no other dNTPs. Since the transponders are individually encoded with the patient's name, several transponders can be placed in the vessel where the reaction takes place.

After the reactions are completed, the transponders are washed 3 times as described above, and dried for 60 minutes at room temperature. The transponders are subjected to the electronic decoding, which is followed by counting of the radioactivity associated with the transponders in a scintillation counter, with or without scintillation fluid. Radioactivity associated with the reaction employing $^3$H dCTP indicates the presence of the mutation in the sample DNA.

TABLE 1

Sequence of exon 1 of the N-ras gene

```
                                         *              50
ATGACTGAGTACAAACTGGTGGTGGTTGGAGC**AGGTGGTGTTGGGAAAAG
TACTGACTCATGTTTGACCACCACCAACCTCGTCCACCACAACCCTTTTC
MetThrGluTyrLysLeuValValValGlyAlaGlyGlyValGlyLysSe
```

TABLE 1-continued

Sequence of exon 1 of the N-ras gene

```
                                                      100
CGCACTGACAATCCAGCTAATCCAGAACCACTTTGTAGATGAATATGATC
GCGTGACTGTTAGGTCGATTAGGTCTTGGTGAAACATCTACTTATACTAG
rAlaLeuThrIleGlnLeuIleGlnAsnHisPheValAspGluTyrAspP

120
CCACCATAGAGgtgaggccc
GGTGGTATCTCcactccggg
roThrIleGlu
```

Legend to Table 1
Bold: Oligonucleotides (1) and (2);
Underlined: oligonucleotide primer (3);
Asterisk—indicates the position of the mutation G→C at codon 12. The sequence is from GenBank 86, entry HNSRAS1.

I claim:

1. A particle for fluorescence assays for nucleic acids comprising:
   (a) a transponder comprising of memory elements, a radio-frequency transmitter and one or more photovoltaic cells, and
   (b) a nucleic acid probe attached directly or indirectly to an outer surface of the transponder, wherein,
      (i) the memory elements contain an index number identifying the particle,
      (ii) the one or more photovoltaic cells provide a source of electrical power for the memory elements and transmitter when illuminated by laser light,
      (iii) the nucleic acid probe specifically binds to said nucleic acid, and
      (iv) fluorescently labeled molecules attached to the particle are detected by measuring fluorescence induced by the laser light.

2. The particle of claim 1, wherein one or more layers of coating are deposited on the outer surface of the transponder and the nucleic acid probe is attached to a coating layer.

3. The particle of claim 2, wherein the layers of coating comprise of glass, latex or plastic.

4. The particle of claim 1, wherein the nucleic acid probe is single stranded.

5. A particle for fluorescence assays for nucleic acids comprising:
   (a) a transponder comprising of memory elements, a radio-frequency transmitter and one or more photovoltaic cells, and
   (b) a layer of streptavidin attached directly or indirectly to an outer surface of the transponder, wherein,
      (i) the memory elements contain an index number identifying the particle,
      (ii) the one or more photovoltaic cells provide a source of electrical power for the memory elements and transmitter when illuminated by laser light, and
      (iii) fluorescently labeled molecules attached to the particle are detected by measuring fluorescence induced by the laser light.

6. The particle of claim 5, wherein a biotinylated nucleic acid probe is bound to the streptavidin layer.

7. A kit for detecting the presence of a nucleic acid in a sample, comprising:
   (A) at least one assay vessel, containing at least one solid phase particle comprising:
      (a) a transponder comprising of memory elements, a radio-frequency transmitter and one or more photovoltaic cells, and
      (b) a nucleic acid probe attached directly or indirectly to an outer surface of the transponder, wherein,
         (i) the memory elements contain an index number identifying the particle,
         (ii) the one or more photovoltaic cells provide a source of electrical power for the memory elements and transmitter when illuminated by laser light,
         (iii) the nucleic acid probe specifically binds to said nucleic acid, and
         (iv) fluorescently labeled molecules attached to the particle are detected by measuring fluorescence induced by the laser light, and
   (B) at least one fluorescent label reagent.

8. The kit of claim 7, wherein the label reagent comprises a reagent that labels the target nucleic acid.

9. The kit of claim 7, wherein the label reagent comprises a second labeled oligonucleotide probe.

10. The kit of claim 7, further comprising:
    (a) at least one positive control, comprising a solution of nucleic acid complementary to the nucleic acid probe bound to the particle, and
    (b) at lease one negative control, comprising a solution free of nucleic acids.

11. The kit of claim 7, further comprising:
    (a) a sample diluent buffer solution, and
    (b) an enzyme reaction buffer solution.

* * * * *